（12） United States Patent
Fattom et al.

(10) Patent No.: US 7,291,343 B2
(45) Date of Patent: *Nov. 6, 2007

(54) ENTEROCOCCUS ANTIGENS AND VACCINES

(75) Inventors: Ali Ibrahim Fattom, Rockville, MD (US); Ramesh K. Sood, Rockville, MD (US); Sara E. Shepherd, Gaithersburg, MD (US)

(73) Assignee: Nabi Biopharmaceuticals, Rockville, MD (US)

( * ) Notice: Subject to any disclaimer, the term of this patent is extended or adjusted under 35 U.S.C. 154(b) by 192 days.

This patent is subject to a terminal disclaimer.

(21) Appl. No.: 10/876,758

(22) Filed: Jun. 28, 2004

(65) Prior Publication Data

US 2005/0008658 A1 Jan. 13, 2005

Related U.S. Application Data

(62) Division of application No. 08/949,757, filed on Oct. 14, 1997, now Pat. No. 6,756,361.

(51) Int. Cl.
*A61K 39/02* (2006.01)
(52) U.S. Cl. ............... 424/234.1; 424/831; 424/134.1; 435/7.32
(58) Field of Classification Search ...................... None
See application file for complete search history.

(56) References Cited

U.S. PATENT DOCUMENTS

| 4,439,422 A | | 3/1984 | Swenson et al. | |
| 4,579,733 A | * | 4/1986 | Kawai et al. | ............ 424/93.44 |
| 4,687,764 A | * | 8/1987 | Kawai et al. | ................. 514/54 |
| 4,692,417 A | * | 9/1987 | Webster | ..................... 435/7.34 |
| 4,695,624 A | | 9/1987 | Marburgh | |
| 4,710,379 A | * | 12/1987 | Kawai et al. | ............ 424/93.44 |
| 4,761,283 A | * | 8/1988 | Anderson | ................ 424/194.1 |
| 4,797,278 A | * | 1/1989 | Kawai et al. | ............ 424/93.44 |
| 4,801,578 A | | 1/1989 | Monsigny | |
| 5,032,505 A | | 7/1991 | Pierce et al. | |
| 5,143,845 A | * | 9/1992 | Masuda | ................... 435/252.4 |
| 5,225,331 A | | 7/1993 | Jennings | |
| 5,478,557 A | * | 12/1995 | Nisbet et al. | ............ 424/93.21 |

(Continued)

FOREIGN PATENT DOCUMENTS

EP 132 981 2/1985

(Continued)

OTHER PUBLICATIONS

Bleiweis, AS et al, J. Bacteriology, Nov. 1967, vol. 94, pp. 1381-1387, Cell Walls of Group D Streptococci.*

(Continued)

*Primary Examiner*—Mark Navarro
*Assistant Examiner*—Ginny Allen Portner
(74) *Attorney, Agent, or Firm*—Foley & Lardner LLP

(57) ABSTRACT

A majority of *E. faecalis* and *E. faecium* clinical isolates fall into two groups and three groups, respectively. Distinct antigens are associate with each of the five groups. The *Enterococcus* antigens are readily obtained from strains of *E. faecalis* and *E. faecium*, and can elicit production of protective antibodies. Accordingly, the antigens are useful for vaccines which protect against infection by clinically significant (pathogenic) *Enterococcus* isolates. The antigens and antibodies generated to the antigens are also useful in diagnostic assays.

24 Claims, 3 Drawing Sheets

U.S. PATENT DOCUMENTS

| | | | |
|---|---|---|---|
| 5,601,999 A * | 2/1997 | Matsuzaki et al. | 435/72 |
| 5,623,057 A | 4/1997 | Marburg et al. | |
| 5,695,768 A | 12/1997 | Malcolm | |
| 5,700,787 A * | 12/1997 | Tzianabos et al. | 514/54 |
| 5,741,495 A * | 4/1998 | Jamas et al. | 424/278.1 |
| 5,760,213 A | 6/1998 | Ooiso et al. | |
| 5,861,157 A * | 1/1999 | Burnie et al. | 424/139.1 |
| 5,871,751 A * | 2/1999 | Christensen et al. | 424/234.1 |
| 5,878,747 A * | 3/1999 | Enomoto et al. | 128/844 |
| 5,989,542 A * | 11/1999 | Pier et al. | 424/93.48 |
| 6,355,625 B1 * | 3/2002 | Pavliak et al. | 514/54 |
| 6,428,793 B1 | 8/2002 | Semprevivo | |
| 6,489,302 B1 | 12/2002 | Wiessler et al. | |
| 6,720,160 B2 * | 4/2004 | Wolde-Mariam | 435/7.32 |
| 6,722,062 B2 * | 4/2004 | Pier et al. | 424/130.1 |
| 6,756,361 B1 * | 6/2004 | Fattom et al. | 514/54 |
| 7,030,101 B2 * | 4/2006 | Pavliak et al. | 514/54 |

FOREIGN PATENT DOCUMENTS

| | | | |
|---|---|---|---|
| JP | 08-027010 | * | 1/1996 |
| RU | 2101029 | * | 1/1998 |
| WO | 87/00531 | * | 1/1987 |
| WO | WO 99/08705 | | 2/1999 |

OTHER PUBLICATIONS

Heidelberger, Michael, Molecular Immunology, vol. 21(11) pp. 1011-1013, 1984, Cross reactions of polysaccharides of staphylococci and streptococci in antipneumonoccal and other bacteria (entire article).*

Kessler, RE et al, Infection and Immunity (1984, reference of record).*

Elliott, SD et al, (1977, reference of record).*

Maekawa, S et al, Microbial Immunol. 1992, vol. 36(7), pp. 671-681, Proposal of a New Schene for the Serological Typing of *Enterococcus faecalis* strains.*

Puzur, JH e tal, The Journal of Biological Chemistry, vol. 246(6), Mar. 25, 1971, pp. 1793-1798, Glycans from Streptococcal Cell Walls( reference of record).*

Hufnagel, Markus et al, Clinical and Diagnostic Laboratory Immunology, Aug. 2005, vol. 12(6), pp. 930-934, Naturally acquired antibodies against Four *Enterococcus faecalis* capsular polysaccharides in Healthy Human sera.*

Supplementary Partial European Search Report No. 98 95 1058, dated Jan. 8, 2003.

Pritchard, David G., et al., "Carbohydrate Fingerprints of Streptococcal Cells," Journal of Clinical Microbiology, Jan. 1981, pp. 89-92, vol. 13, No. 1.

Fattom, Ali, et al., "Laboratory and Clinical Evaluation of Conjugate Vaccines Composed of Staphylcoccus Aureus Type 5 and Type 8 Capsular Polysaccharides Bound to *Pseudomonas aeruginosa* Recombinant Exoprotein A," Infection and Immunity, Mar. 1993, pp. 1023-1032, vol. 61, No. 3.

Naso, Robert, et al. "Polysaccharide Conjugate Vaccines for the Prevention of Gram-Positive Bacterial Infections," Advances in Experimental Medicine and Biology, pp. 133-140, vol. 397, 1996.

Heidelberg, M., Molecular Immunology, Nov. 1984, vol. 21(11), pp. 1011-1013, (abstract).

Pazur, JH et al., Journal of Immunological Methods, Dec. 14, 1984, vol. 75(1), pp. 107-116 (abstract only).

Yakushiji, K.K. et al., Oral Microbial Immunology, vol. 8, pp. 161-166, 1993.

Naso, R. et al., Advances in Experimental Medicine and Biology, vol. 397, pp. 133-138 (abstract), date unknown.

Moreau, M. et al., Oct. 15, 1988, Carbohydrate Res., vol. 182(1), pp. 79-99.

Wessman, GE, Infection Immunity, Jul. 1975, vol. 12(1), pp. 156-161.

Aluyi, HS et al, J. Appl. Bacteriol., Jun. 1983, vol. 54(3), pp. 391-397.

Pazure, J.H. et al., Glycans from Streptococcal Cell Walls, The Journal of Biological Chemistry, Mar. 25, 1971, vol. 246, No. 6, pp. 1793-1798, see abstract and entire document.

Amvam-Zollo, P. et al., Streptococcus pneumoniae type XIV polysaccharide: synthesis of a repeating branched tetrasaccharide with dioxa-type spacer-arms, Carbohydrate Research, 1986, vol. 150, pp. 199-212.

Guzman, C.A. et al. Serum Dependent Expression of *enterococcus faecalis* adhesions involved in the colonization of heart cells; Microbial Pathology, 1991, vol. 11, No. 60, pp. 399-409, p. 406, 1st paragraph.

Kessler, R.E., Interaction of anti-kojibiose antibody with the lipoteichoic acids from *Streptococcus faecalis* and *Streptococcus faecium*; Infection and Immunity; 10/19 vol. 46, No. 1, pp. 279-281, see entire doc.

Pazur, J.H. et al., Determination of the sugar sequences and the glycosidic-bond arranges of immunogenic heteroglycans, Carbohydrate Research, 1978, vol. 60, pp. 167-178, No. 1, especially abstract.

Elliott, S.D. et al., Telchoic Acids of Group D Streptococci with special reference to strains from pig meningitis, Journal of Experimental Medicine, 1977, vol. 145, No. 3, pp. 490-499, especially 499, first paragraph 2.

Dick, W.E., Jr et al., Glycoconjugates of bacterial carbohydrate antigens, Contributions to Microbiology and Immunology, Conjugate vaccines, 1989, vol. 10, pp. 48-114, see entire document.

* cited by examiner

ENTEROCOCCUS ANTIGENS AND VACCINES

CROSS-REFERENCE TO RELATED APPLICATIONS

This application is a division of U.S. application Ser. No. 08/949,757, filed Oct. 14, 1997, now U.S. Pat. No. 6,756,361.

BACKGROUND OF THE INVENTION

The present invention relates to antigens from *Enterococcus* that are useful as vaccines, and to methods for obtaining and using such antigens.

The prevalence of *Enterococcus* infection is increasing steadily. Strains of *Enterococcus* now are responsible for 12% of all the nosocomial infections among hospitalized patients and they are the second most common organism isolated from patients with nosocomial infections. This increased prevalence of *Enterococcus* is due at least in part to the appearance of strains of enterococci that are resistant to antimicrobial agents and therefore difficult to treat with currently available antibiotics. The increase in antibiotic resistance among *Enterococcus* has increased the importance of alternative prophylactic and therapeutic approaches against enterococcal infections.

Various groups have disclosed polysaccharides isolated from *Enterococcus*. For example, lipoteichoic acids which contain a 1,3-linked polyglycerophosphate backbone have been isolated from "*S. faecalis*," which according to current classification is *E. faecalis*. Position 2 is glycosylated with disaccharides or trisaccharides of glycosyl residues which may be esterified with alanyl residues, and is denoted intracellular teichoic acid because of its predominance between the cell wall and the protoplast membrane. Wicken et al., *J. Gen. Microbiol.* 33: 231-39 (1963).

Pazur et al., *J. Biol. Chem.* 246: 1793-98 (1971), have isolated two other polysaccharides from the cell wall of *E. faecalis* strain N. One of these polysaccharides is characterized as a diheteroglycan consisting of glucose and D-galactose, while the other polysaccharide is said to be a tetraheteroglycan of 2-acetamide-2-deoxy-galactose, galactose, rhamnose, and glucose in molar ratio of 1:1:2:4.

Bleiweis et al., *J. Bacteriol.* 94: 1381-87 (1967), have isolated a third polysaccharide from strain D76 of group D Streptococci. The sugar composition of this material includes glucose, glucosamine, galactosamine, rhamnose, ribitol, and phosphorus; structural information is not provided, however. It is postulated that this material may be ribitol phosphate teichoic acid with attached sugar substituents. It also has been hypothesized that glucose and N-acetyl glucosamine are the possible components of the antigenic site.

*Enterococcus* antigen(s) capable of eliciting protective antibodies would provide an effective means of preventing and/or treating *Enterococcus* infection. While the art discloses a variety of *Enterococcus* antigens, not every antigen is effective as a vaccine. Indeed, none of the material reported in the literature has been shown to be effective in protecting against infection by *Enterococcus*. In this regard, even a disclosure that an antigen is immunogenic, i.e., that it causes the production of antibodies, provides an insufficient basis for a conclusion that the antibodies are protective and that the antigen therefore is useful in a vaccine.

Finally, the art suggests that *Enterococcus* serologically is a very diverse genus. This serologic diversity suggested that a vaccine comprised of a practical number of active components was not feasible. Maekawa et al., *Microbiol. Immunol.* 36: 671-681 (1992).

SUMMARY OF THE INVENTION

It is therefore an object of the present invention to provide *Enterococcus* antigens, particularly antigens from *E. faecalis* and *E. faecium*, that are capable of eliciting the production of protective antibodies.

It is a further object to provide a vaccine that contains *Enterococcus* antigens, more particularly a vaccine that contains antigens from both *E. faecalis* and *E. faecium*.

It is another object to provide a hyperimmune globulin composition that contains antibodies directed against *Enterococcus* antigens, particularly antigens from *E. faecalis* and *E. faecium*.

In accordance with these and other objects according to the invention, there is provided an isolated *Enterococcus* antigen that reacts with antibodies to cells from one of ATCC 202013, ATCC 202014, ATCC 202015, ATCC 202016, and ATCC 202017. More particularly, an isolated *Enterococcus* antigen is selected from the group consisting of an *E. faecalis* antigen comprising 2-acetamido-2-deoxy-glucose and rhamnose in an approximate 1:2 molar ratio, an *E. faecalis* antigen comprising a trisaccharide repeat which comprises a 6-deoxy sugar, and an *E. faecium* antigen comprising 2-acetamido-2-deoxy-galactose and galactose.

The antigen can be used in diagnostic assays or in immunotherapy methods. A conjugate in which the antigen is covalently bonded to an immunocarrier, preferably a recombinantly-produced, non-toxic mutant strain of *Pseudomonas aeruginosa* exotoxin A or diphtheria toxoid, is provided. The antigen-carrier conjugates are useful in a vaccine, particularly a multivalent vaccine, for active immunotherapy. The antigen or vaccine also can be used to produce immune globulin for passive immunotherapy, or in the production of monoclonal antibodies for diagnostic or therapeutic use.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

Figure 1:
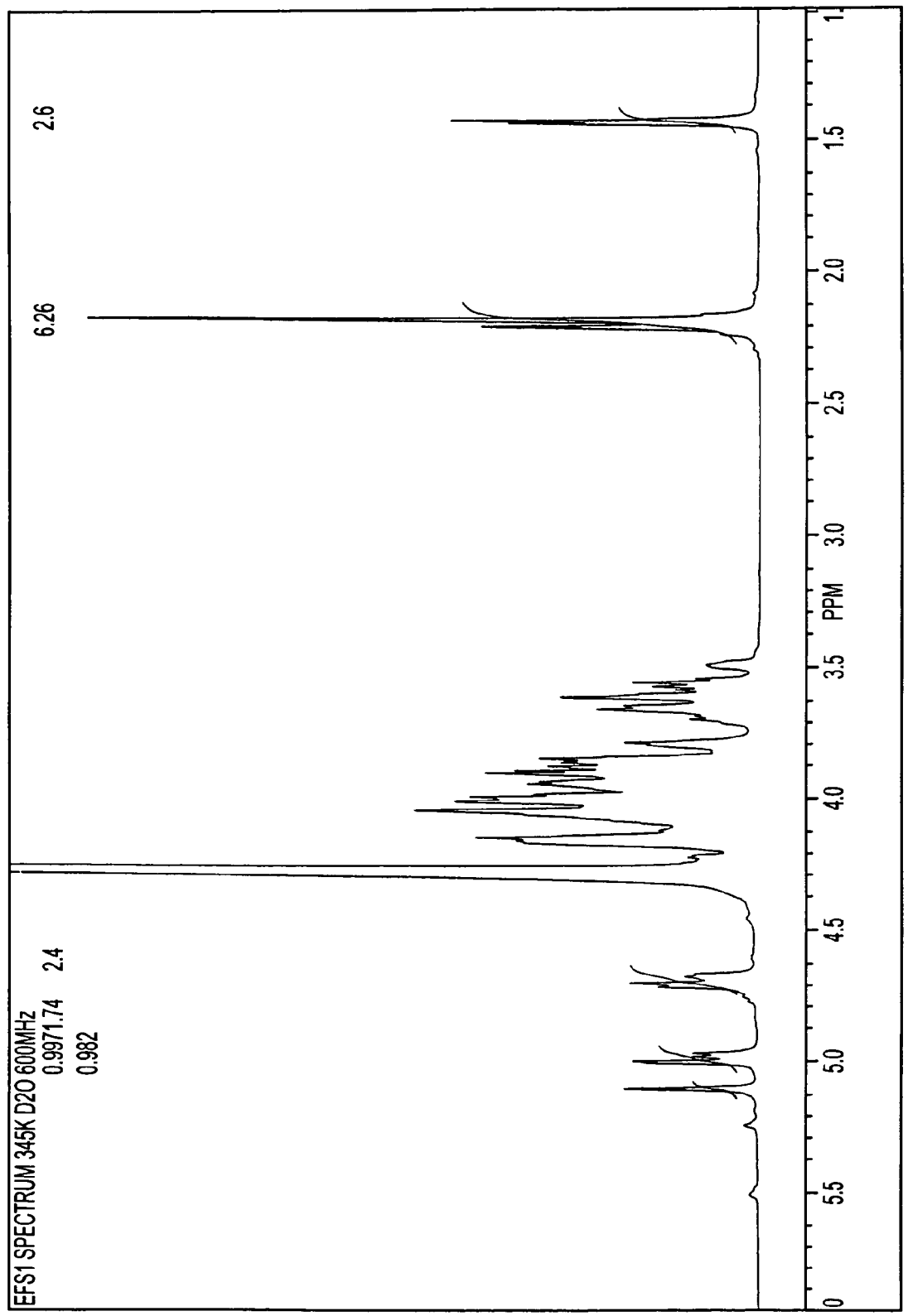
FIG. 1, 2 and 3 are NMR spectra for *Enterococcus* antigens according to the invention.

It surprisingly has been discovered that the majority of *E. faecalis* clinical isolates fall into two groups, and that the majority of *E. faecium* human clinical isolates fall into three groups. The discovery that the majority of clinical isolates are characterized by only a few common antigens is unheralded in the art, and permits development of multivalent vaccines that comprise a minimal number of active components yet are protective against the majority of clinical isolates.

Antigens characteristic of each of the two groups of *E. faecalis* and three groups of *E. faecium* can be extracted, purified and identified. In this regard, an antigen is characteristic of a group or strain of bacteria if it is expressed by the bacteria in a quantity sufficient to cause a significant immune response when a whole cell vaccine of the group or strain is injected into an animal, i.e., an animal produces protective antibodies when so injected.

The *E. faecalis* characteristic antigens are denoted herein as EFS1 and EFS2, and the *E. faecium* characteristic antigens as EFM3, EFM4 and EFM5. These antigens are referred to collectively herein as "*Enterococcus* antigens." A strain of bacteria is called an EFS1 strain if a whole cell vaccine of the strain produces a significant immune response primarily toward EFS1 when injected into a subject, and only a minor response to EFS2. Similarly, a strain of bacteria is called an EFS2 strain if a whole cell vaccine of the strain produces a significant immune response primarily toward EFS2 when injected into a subject, and so forth.

While each of the major clinical groups of *E. faecalis* and *E. faecium* expresses a different characteristic antigen that may be readily extracted and purified in recoverable amount, the groups also may express antigen characteristic of the other group(s) in minor amounts. However, when immunized with whole cells from one of the groups, rabbits mount a significant immune response only toward the characteristic antigen of that group, and not at all or only poorly to the minor amounts of the antigen most characteristic of the other group(s), as shown by the absence of a precipitin band between antibodies from the immunized rabbit and purified antigen characteristic of the other group.

The degree to which a non-characteristic antigen is expressed by cells varies. For example, antisera generated against a whole cell vaccine of an EFS1 strain contains antibodies to EFS2 in amounts, detectable both by slide agglutination and by opsonophagocytosis assay (infra). Antisera generated against a whole cell vaccine of an EFS2 strain, on the other hand, does not contain antibodies that precipitate with EFS1.

The *Enterococcus* antigens are readily obtained from strains of *E. faecalis* and *E. faecium*, pursuant to protocols provided herein, and are capable of eliciting production of protective antibodies when conjugated to immunocarriers. They therefore can be used to prepare vaccines that provide protection of humans and other mammals, e.g., horses, cattle, swine, dogs, and cats, against infection by clinically significant isolates of *Enterococci*. In this regard, a "clinically significant" isolate is one that is pathogenic in humans or other mammals.

*E. faecalis* and *E. faecium* clinical isolates can be grouped by slide agglutination experiments, using an appropriate antibody preparation for agglutination of bacteria. Slide agglutination experiments with *E. faecalis* show that the majority of clinical isolates fall into two groups, EFS1 and EFS2. Antisera generated against an EFS1 strain of *E. faecalis* agglutinates both EFS1 and EFS2 strains of *E. faecalis*. The reactivity of antisera generated against an EFS1 strain of *E. faecalis* can be absorbed out with cells from the EFS1 strain. The absorbed sera may then continue to agglutinate only an EFS2 strain.

Antisera generated against an EFS2 strain of *E. faecalis* agglutinates only EFS2 strains, and this reactivity cannot be absorbed out with EFS1 bacteria. As expected, absorption with cells from an EFS2 strain removes the reactivity of this antisera with cells from an EFS2 strain. While not wishing to be bound by theory, it is hypothesized that EFS1 and EFS2 strains of *E. faecalis* contain EFS2 antigen, but that this antigen is covered or otherwise masked by EFS1 antigens on EFS1 cells.

Slide agglutination experiments with *E. faecium* show that the majority of clinical isolates fall into three groups. Antisera raised against two of the groups give results similar to that obtained with *E. faecalis*. That is, antisera generated against a EFM3 strain of *E. faecium* agglutinates both EFM3 and EFM5 bacteria, and the reactivity of this antisera with an EFM3 strain can be absorbed out with cells from an EFM3 strain. The absorbed sera then agglutinates only EFM5 strains of bacteria. This absorption also causes a reduction in reactivity with cells from EFM5 strains, indicating that small amounts of EFM5 antigen is exposed on the surface of EFM3 cells.

Antisera generated against a EFM5 strain of *E. faecium* agglutinates only isolates in that group, and this reactivity cannot readily be absorbed out with cells of an EFM3 strain. As expected, absorption with cells from an EFM5 strain reduces the reactivity of this antisera with cells. Similarly EFM3 and EFM5 strains of *E. faecium* both contain EFM5 antigen. Again, this antigen is hypothesized to be covered or otherwise masked by EFM3 antigen on EFM3 cells.

Antisera raised against an EFM4 strain of *E. faecium* is specific only to cells of EFM4 strains in slide agglutination experiments. This antisera demonstrates no cross reactivity with EFM3 and EFM5 bacteria.

Antibodies generated against the whole cell vaccine generally are not directed toward proteins on the cell surface, as shown by treatment of formalin-killed cells with pronase E. When killed cells are incubated for 3 hours at 37° C. with 500 μg/ml pronase E, and then tested in slide agglutination against whole cell sera, there is no difference in the agglutination pattern from that observed with untreated *E. faecium* or *E. faecalis*, i.e., the pronase treatment does not remove the surface antigen against which the antibodies are directed.

Representatives of each of the two *E. faecalis* and three *E. faecium* strains have been deposited under the Budapest Treaty with the American Type Culture Collection (P.O. Box 1549, Manassas, Va. 20108) on Aug. 13, 1997 and have been accorded Accession Nos. 202013 (*E. faecalis* EFS1), 202014 (*E. faecalis* EFS2), 202015 (*E. faecium* EFM3), 202016 (*E. faecium* EFM4), and 202017 (*E. faecium* EFM5) respectively. Antigen according to the invention can be isolated from the deposited strains, or the deposited strains can be used to identify other strains which express antigen according to the invention, from which antigen may be extracted and purified in accordance with protocols described herein.

*Enterococcus* antigens according to the invention can be obtained in recoverable amount, and in substantially pure form, from their respective *E. faecalis* and *E. faecium* isolates cultured pursuant to the protocols described herein. A "recoverable" amount in this regard means that the isolated amount of the antigen is detectable by a methodology less sensitive than radiolabeling, such as immunoassay, and can be subjected to further manipulations involving transfer of the antigen per se into solution.

In an illustrative approach to obtaining antigen according to the present invention, a strain of *E. faecalis* or *E. faecium* first is grown on a blood agar plate and then transferred to a 2% NaCl/Columbia starter flask. An 80-liter fermentor that contains the same medium with added 4% glucose is inoculated with the starter flask. Cells are fermented for 16-24 hours. The cells were centrifuged to separate the cells from the supernatant. Each of the five antigens can be extracted from either cell paste or supernatant.

When cell paste is used, antigen is extracted by stirring the paste with cold 10% trichloroacetic acid (TCA), and then precipitated from the TCA solution by one or more sequential precipitations with cold ethanol/$CaCl_2$. When supernatant is used, the supernatant is subjected directly to precipitation with cold ethanol/$CaCl_2$. This produces a crude antigen extract.

The crude extract is redissolved in water, dialyzed and lyophilized. The lyophilized material is dissolved in buffer and purified by ion exchange chromatography. Fractions containing antigen can be pooled, dialyzed, concentrated, and lyophilized, and size exclusion chromatography is used to purify the antigen further by size on a suitable column. Antigen-containing fractions are pooled, concentrated, dialyzed and lyophilized. Purified antigen is analyzed by $^1$H-NMR spectroscopy.

A composition of the *Enterococcus* antigen according to the present invention "consists essentially of" the antigen(s) or a conjugate of the antigen(s), which means that the composition does not contain any material that interferes with elicitation of an immune response to the antigen(s) when the composition is used in a therapeutic context, or with the antigen-antibody coupling characteristic of a diagnostic assay. In a preferred embodiment, the composition contains both *E. faecalis* and *E. faecium* antigens.

The antigens according to the invention are useful in the production of diagnostic assays for detecting the presence of *Enterococcus* antigen and/or anti-*Enterococcus* antibody in a sample. Either the *Enterococcus* antigen or antibody specific to the *Enterococcus* antigen is mixed with a sample suspected of containing *Enterococcus* antibody or antigen and monitored for antigen-antibody binding. The antigen or antibody is labelled with a radioactive or enzyme label. In a preferred embodiment, the antigen or antibody is immobilized on a solid matrix such that the antigen or antibody is accessible to complementary antibody or antigen contacting a surface of the matrix. The sample then is brought into contact with the surface of the matrix, and the surface is monitored for antigen-antibody binding.

For example, the antigen or antibody can be used in an enzyme-linked immunosorbent assay (ELISA), in which antigen or antibody is bound to a solid phase and an enzyme-antibody or enzyme-antigen conjugate is used to detect and/or quantify antibody or antigen present in a sample. Alternatively, a western blot assay can be used in which solubilized and separated antigens are bound to nitrocellulose paper. The antibody then is detected by an enzyme or label-conjugated anti-immunoglobulin (Ig), such as horseradish peroxidase-Ig conjugate by incubating the filter paper in the presence of a precipitable or detectable substrate. Western blot assays have the advantage of not requiring purity greater than 50% for the desired antigen. Descriptions of ELISA and western blot techniques are found in Chapters 10 and 11 of Ausubel, et al. (eds.), CURRENT PROTOCOLS IN MOLECULAR BIOLOGY, John Wiley and Sons (1988), the contents of which are hereby incorporated by reference.

In a vaccine context, it is preferable to conjugate the antigen(s) to an immunocarrier, usually a polypeptide or protein, to improve the interaction between T and B cells for the induction of an immune response against the antigen. This is particularly important for vaccines intended for use in patients with reduced resistance. An immunocarrier enhances immunogenicity both for active immunization and for preparing high-titered antisera in volunteers for passive immunization. Suitable immunocarriers according to the present invention include tetanus toxoid, diphtheria toxoid, *Pseudomonas aeruginosa* Exotoxin A or its derivatives, recombinantly-produced non-toxic mutant strains of exotoxin A, as described, for example, in Fattom et al., *Inf. and Imm.* 61: 1023-32 (1993), as well as other proteins commonly used as immunocarriers.

In order to conjugate the antigen to a carrier, the antigen is first derivatized. Various methods can be used to derivatize antigen and covalently link it to an immunocarrier. In a preferred method, hydroxyl groups on the antigen are activated using 1-cyano-4-dimethylamino-pyridinium tetrafluoroborate, and the antigen is then derivatized with a six carbon bifunctional spacer adipic acid dihydrazide (ADH), according to techniques known in the art, according to the method of Kohn et al. *FEBS Lett.* 154: 209:210 (1993). This material is then linked to diphtheria toxoid (DT), recombinant exoprotein A from Pseudomonas aeruginosa (rEPA), tetanus toxoid (TT) or another suitable carrier protein by 1-ethyl-3-(3-dimethylaminopropyl) carbodiimide (EDAC). The resulting conjugates can be separated from unreacted antigen by size exclusion chromatography.

Preferably the antigen conjugate is administered with an adjuvant which promotes the protective IgG subtype 2 antibodies. Typical adjuvants include complete Freund's adjuvant (CFA), incomplete Freund's adjuvant (IFA), alum and other adjuvants suitable for human and animal use. Dextran sulfate has been shown to be a potent stimulator of $IgG_2$ antibody against staphylococcal cell surface antigens, and also is suitable as an adjuvant.

Induction of bacteremia in some mammals, e.g., laboratory animals, requires extremely high numbers of organisms or some previous maneuver to lower the host resistance. In vitro phagocytosis, however, can be studied as a correlate of protective immunity in vivo for humans and other mammals. In this model, the ability of antigen-specific monoclonal and polyclonal antibodies to opsonize *Enterococcus* strains in vitro is measured by phagocytosis, according to the method described in Kojima et al., *Infect. Dis. Immun.* 58: 2367-74 (1990). In vitro opsonophagocytosis assays are recognized in the field as being predictive of efficacy as a vaccine. For example, Fischer et al. discloses a correlation between functional antibody determined with an in vitro opsonic assay and in vivo activity. *J. Inf. Dis.* 169: 324-9 (1994).

Antibodies induced by the *Enterococcus* antigens according to the invention are opsonic and facilitate type-specific phagocytosis. Rabbit antibodies raised against the *Enterococcus* antigens are able specifically to mediate the opsonophagocytosis of the strains carrying the antigens by human polymorphonuclear leukocytes (PMN) cells in the presence of human complement. The in vitro phagocytosis assays thus indicate that antibodies to the *Enterococcus* antigens are protective against infection by *E. faecalis* and *E. faecium*. A vaccine based on a combination of *E. faecalis* and *E. faecium* antigens can be used to protect against infection from the majority of clinical *Enterococcus* strains.

In vivo results are consistent with results of in vitro opsonophagocytosis assays. Antibodies to EFS1 conjugate lowered bacteremia in mice challenged with *E. faecalis*.

The present invention also relates to the use of the *Enterococcus* antigen(s) to produce polyclonal antibodies or monoclonal antibodies (mouse or human) that bind to or neutralize *Enterococcus*. Illustrative protocols for producing these antibodies are described in Chapter 11 of MOLECULAR CLONING: A LABORATORY MANUAL, Cold Spring Harbor Laboratory (Cold Spring Harbor, N.Y.); in METHODS OF HYBRIDOMA FORMATION 257-271, Humana Press (Clifton, N.J.); in Vitetta et al., *Immunol. Rev.* 62: 159-83 (1982); and in Raso, *Immunol. Rev.* 62: 93-117 (1982).

Inoculum for polyclonal antibody production typically is prepared by dispersing the antigen-immunocarrier in a physiologically-tolerable diluent such as saline, to form an aqueous composition. An immunostimulatory amount of inoculum, with or without adjuvant, is administered to a mammal, and the inoculated mammal then is maintained for a time period sufficient for the antigen to induce protecting anti-*Enterococcus* antigen antibodies. Boosting doses of the antigen-immunocarrier may be used in individuals that are not already primed to respond to the antigen.

Antibodies can include antibody preparations from a variety of commonly used animals, such goats, primates, donkeys, swine, rabbits, horses, hens, guinea pigs, rats, and mice, and even human antibodies after appropriate selection, fractionation and purification. Animal antisera may also be raised by inoculating the animals with formalin-killed strains of *E. faecalis* and/or *E. faecium* by conventional methods, bleeding the animals and recovering serum or plasma for further processing.

The antibodies induced in this fashion can be harvested and isolated to the extent desired by well known techniques, such as by alcohol fractionation and column chromatography, or by immunoaffinity chromatography; that is, by binding antigen to a chromatographic column packing like Sephadex™, passing the antiserum through the column, thereby retaining specific antibodies and separating out other immunoglobulins (IgGs) and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the sera or plasma of humans that have developed an antibody titer against the pathogen in question, thus assuring the retention of antibodies that are capable of binding to the antigen. They can then be used in preparations for passive immunization against strains of *E. faecalis* and *E. faecium*.

A monoclonal antibody composition contains, within detectable limits, only one species of antibody combining site capable of effectively binding to the *Enterococcus* antigen. Suitable antibodies in monoclonal form can be prepared using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with the *Enterococcus* antigen. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred myeloma being P3X63-Ag8.653. The preferred fusion partner for human monoclonal antibody production is SHM-D33, a heteromyeloma available from ATCC, Rockville, Md. under the designation CRL 1668.

A monoclonal antibody composition of the present invention can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are both well known in the art and commercially available, and include synthetic culture media, inbred mice and the like. An exemplary synthetic medium is Dulbecco's Minimal essential medium supplemented with 20% fetal calf serum. An exemplary inbred mouse strain is the Balb/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the *Enterococcus* antigen. More preferable in this regard, however, is a process that does not entail the use of a biological sample from an infected human subject. For example, a subject immunized with a vaccine as described herein can serve as a source for antibodies suitably used in an antibody composition within the present invention. Purified monoclonal antibodies can be characterized by bacterial agglutination assays using a collection of clinical isolates, or by ELISA using plates coated with purified antigen.

The monoclonal and polyclonal antibody compositions produced according to the present description can be used by passive immunization to induce an immune response for the prevention or treatment of infection by strains of *E. faecalis* and *E. faecium*. In this regard, the antibody preparation can be a polyclonal composition. Such a polyclonal composition includes antibodies that bind to the *Enterococcus* antigen(s). The polyclonal antibody component can be a polyclonal antiserum, preferably affinity purified, from an animal which has been challenged with the *Enterococcus* antigen(s). Alternatively, an "engineered oligoclonal" mixture may be used, which is a mixture of monoclonal antibodies to the *Enterococcus* antigens from both *E. faecalis* and *E. faecium*.

In both types of mixtures, it can be advantageous to link antibodies together chemically to form a single polyspecific molecule capable of binding to both *E. faecalis* and *E. faecium* antigens. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, LABELED ANTIBODIES IN BIOLOGY AND MEDICINE 321-23, McGraw-Hill Int'l Book Co. (1978); Nisonoff et al., *Arch Biochem. Biophys.* 93: 470 (1961); and Hammerling et al., *J. Exp. Med.* 128: 1461 (1968); and in U.S. Pat. No. 4,331,647.

Other methods are known in the art to make bivalent fragments that are entirely heterospecific, for example, use of bifunctional linkers to join cleaved fragments. Recombinant molecules are known that incorporate the light and heavy chains of an antibody. See, for instance, the products of a methodology described by Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art.

An antibody component produced in accordance with the present invention can include whole antibodies, antibody fragments, or subfragments. Antibodies can be whole immunoglobulin of any class, e.g., IgG, IgM, IgA, IgD, IgE, chimeric antibodies or hybrid antibodies with dual or multiple antigen or epitope specificities, or fragments, e.g., F(ab')$_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like E. coli. A lambda vector system is available thus to express a population of Fab's with a potential diversity equal to or exceeding that of subject generating the predecessor antibody. See Huse, W.D., et al., Science 246: 1275-81 (1989).

Antigen conjugate(s) according to the present invention can be the active ingredient in a composition, further comprising a pharmaceutically acceptable carrier for the active ingredient, which can be used as a vaccine to induce a cellular immune response and/or production in vivo of antibodies which combat Enterococcus infection. In this regard, a pharmaceutically acceptable carrier is a material that can be used as a vehicle for administering a medicament because the material is inert or otherwise medically acceptable, as well as compatible with the active agent, in the context of vaccine administration. In addition to a suitable excipient, a pharmaceutically acceptable carrier can contain conventional vaccine additives like diluents, adjuvants, antioxidants, preservatives and solubilizing agents.

Pursuant to the present invention, such a vaccine can be administered to a subject not already infected with E. faecalis or E. faecium, thereby to induce a Enterococcus-protective immune response (humoral or cellular) in that subject. Alternatively, a vaccine within the present invention can be administered to a subject in which E. faecalis and/or E. faecium infection already has occurred but is at a sufficiently early stage that the immune response produced to the vaccine effectively inhibits further spread of infection.

By another approach, a vaccine of the present invention can be administered to a subject who then acts as a source for immune globulin, produced in response to challenge from the specific vaccine that contains antibodies directed against Enterococcus. A subject thus treated would donate plasma from which immune globulin would then be obtained, via conventional plasma-fractionation methodology, and administered to another subject in order to impart resistance against or to treat Enterococcus infection. Immune globulins according to the invention are particularly useful for immune-compromised individuals, for individuals undergoing invasive procedures or where time does not permit the individual to produce his own antibodies in response to vaccination.

Similarly, monoclonal or polyclonal anti-Enterococcus antibodies produced according to the present invention can be conjugated to an immunotoxin, and administered to a subject in whom Enterococcus infection has already occurred but has not become widely spread. To this end, antibody material produced pursuant to the present description would be administered in a pharmaceutically acceptable carrier, as defined herein.

The present invention is further described by reference to the following, illustrative examples.

EXAMPLE 1

Fermentation of E. faecalis and E. faecium

E. faecalis and E. faecium were cultivated in Columbia broth supplemented with 2% NaCl and 4% glucose in an 80-liter fermentor containing 60 liters of broth medium at 37° C. The fermentation was started with one liter of a 16 hour old seed culture. The cells were grown with agitation at 200 rpm for 16-24 hours.

Cells to be used as a vaccine to prepare whole cell antiserum were formalin fixed overnight at room temperature. Cells for purification were harvested by centrifugation at 14,500×g and stored at −70° C. until use. Approximately 500 g, 180 g, and 350 g of cell paste (net weight) were obtained from an 80-liter fermentor for EFS1, EFS2 and EFM3, respectively.

EXAMPLE 2

Preparation of Whole Cell Antiserum

Killed and formalin-fixed cells from two strains of E. faecalis and three strains of E. faecium cultivated as in Example 1 were adjusted at OD$_{540\ nm}$=1 and were injected intravenously into rabbits. No adjuvant was used. The rabbits received 10 injections and were bled at weekly intervals after the last injection and positive whole cell serum was collected and pooled. IgG was purified from whole cell serum by a protein G affinity column.

EXAMPLE 3

Agglutination Studies with E. faecalis and E. faecium

Immune rabbit sera obtained from rabbits immunized with the two killed and formalin-fixed strains of E. faecalis and three killed and formalin-fixed strains of E. faecium were used to type isolates of E. faecalis and E. faecium by slide agglutination. The antisera were used to type 67 clinical isolates of E. faecalis and 85 clinical isolates of E. faecium. Sixty of the 67 isolates of E. faecalis (89.5%) reacted with antisera obtained by immunization of rabbits with cells of ATCC 202013. Forty-one of the 85 clinical isolates of E. faecium reacted with antisera obtained by immunization of rabbits with cells of ATCC 202015.

EXAMPLE 4

Antigen Purification

Based on the results reported in Example 3, antigens were isolated from ATCC 202013, ATCC 202014, and ATCC 202015, respectively. Antigens were extracted from cell paste or from supernatant obtained according to Example 1.

Purification of EFS1 Antigen

This antigen was isolated from the cell paste of ATCC 202013. The antigen was extracted from the cell surface by stirring the cell paste (434 g) with cold 10% TCA (1735 ml) at 4° C. for a period of 48 hours. A clear supernatant was obtained by centrifugation. This supernatant was concentrated to its original ⅕th volume by evaporation under reduced pressure below 40° C. An equal volume of 95% ethanol was added to this solution and the solution was incubated at 4° C. overnight. A small amount of precipitates was separated from the supernatant by centrifugation.

Another four volumes of ethanol were added to the clear supernatant and a sufficient amount of 1 M CaCl$_2$ was added to make a final 10 mM CaCl$_2$ concentration in the solution. The mixture was incubated again at 4° C. overnight. The precipitates were recovered by centrifugation.

The precipitates were redissolved in a minimum amount of cold 10% TCA and the above 50% and 80% ethanol precipitation steps were repeated to remove more impurities. Final precipitates recovered after 80% ethanol precipitation step were dissolved in water, dialyzed against cold distilled water and lyophilized. This material was dissolved in 0.01 M Tris-HCl buffer, pH 7.0, and loaded on to Q-Sepharose anion exchange column. The column was eluted sequentially with 0.01 M Tris-HCl buffer containing 0.1 and 0.2 M NaCl. The 0.2 M NaCl fraction was dialyzed against cold distilled water and lyophilized. The lyophilized material was further purified on Sephacryl S-300 column and eluted with phosphate buffered saline (PBS) to obtain 258 mg of the final purified antigen.

Purification of EFS2 Antigen

Antigen was purified from the supernatant obtained from the fermentation of ATCC 202014. Crude material was obtained from the supernatant by 25-75% ethanol precipitation containing 10 mM CaCl$_2$. The fraction obtained from the 75% ethanol precipitation was partially purified by ion exchange chromatography on a Q-Sepharose column. The column was eluted sequentially with 0.01 M Tris-HCl buffer containing 0.2 and 0.5 M NaCl. The 0.5 M NaCl fraction was treated with protease overnight to remove contaminating proteins and subsequently further purified by size exclusion chromatography on a Sephacryl S-300 column. The fractions reacting with whole cell antisera to ATCC 202014 were pooled and further purified by a second ion exchange step on a Q-Sepharose column. The material was eluted with a linear 0.2-0.5 M sodium chloride gradient in Tris-HCl buffer at pH 7. The same material also was isolated from the cells following similar steps after the release of this material from the cell surface by chemical or enzymatic treatment.

Purification of EFM3 Antigen

Antigen was extracted from ATCC 202015 by stirring the cell paste with cold 10% TCA at 40° C. for 48 hours, as described for EFS1. A clear supernatant was obtained by centrifugation. This supernatant was concentrated to its original ⅕th volume by evaporation under reduced pressure below 40° C. An equal volume of 95% ethanol was added to this solution and the solution was incubated at 4° C. overnight. A small amount of precipitates was separated from the supernatant by centrifugation. Another four volumes of ethanol were added to the clear supernatant, and a sufficient amount of 1 M CaCl$_2$ was added to make a final 10 mM CaCl$_2$ concentration in the solution. The mixture was incubated again at 4° C. overnight. The precipitates were recovered by centrifugation.

The precipitates were redissolved in a minimum amount of cold 10% TCA and the above 50% and 80% ethanol precipitation steps were repeated to remove more impurities. Final precipitates recovered after 80% ethanol precipitation step were dissolved in 0.01 M Tris-HCl buffer, pH 7.0, and loaded on to Q-sepharose anion exchange column. The column was eluted by the above buffer containing 0.1 M NaCl. The fraction was dialyzed against cold distilled water and lyophilized. The lyophilized material was further purified on a Sephacryl S-300 column and eluted with PBS. Antigen-containing fractions were pooled, dialyzed against cold distilled water and lyophilized.

EXAMPLE 5

Antigen Characterization

The antigens isolated in Example 4 were analyzed to determine their composition. EFS1 comprises major amounts of four sugars: 2-acetamido-2-deoxy-glucose, rhamnose, glucose and 2-acetamido-2-deoxy-galactose in an approximate calculated molar ratio of 1:2:2:2. A complete biochemical analysis of the antigen is given in Table 1.

TABLE 1

| EFS1 | |
|---|---|
| Assay performed | Result |
| Phenol-sulfuric acid | 25-41% |
| Phosphorus | 1.5-2.5% |
| Residual nucleic acid | <1% |
| Residual protein | <1% |
| Uronic acid | undetectable |
| O-acetyl | undetectable |

The material also was analyzed by H$^1$-NMR spectroscopy. The major down field peaks observed were at δ 5.14 (s), 5.03 (s), 5.01 (d, J$_{1,2}$=7.8 Hz), 4.78-4.67 (complex). In the high field region the spectrum showed resonances at 2.21 and 2.18 due to N-acetyl groups, and at 1.43 (d, J$_{5,6}$=6Hz) due to the 6-methyl group of the 6-deoxy sugar. A complete spectrum of the material is shown in FIG. 1.

Figure 2:
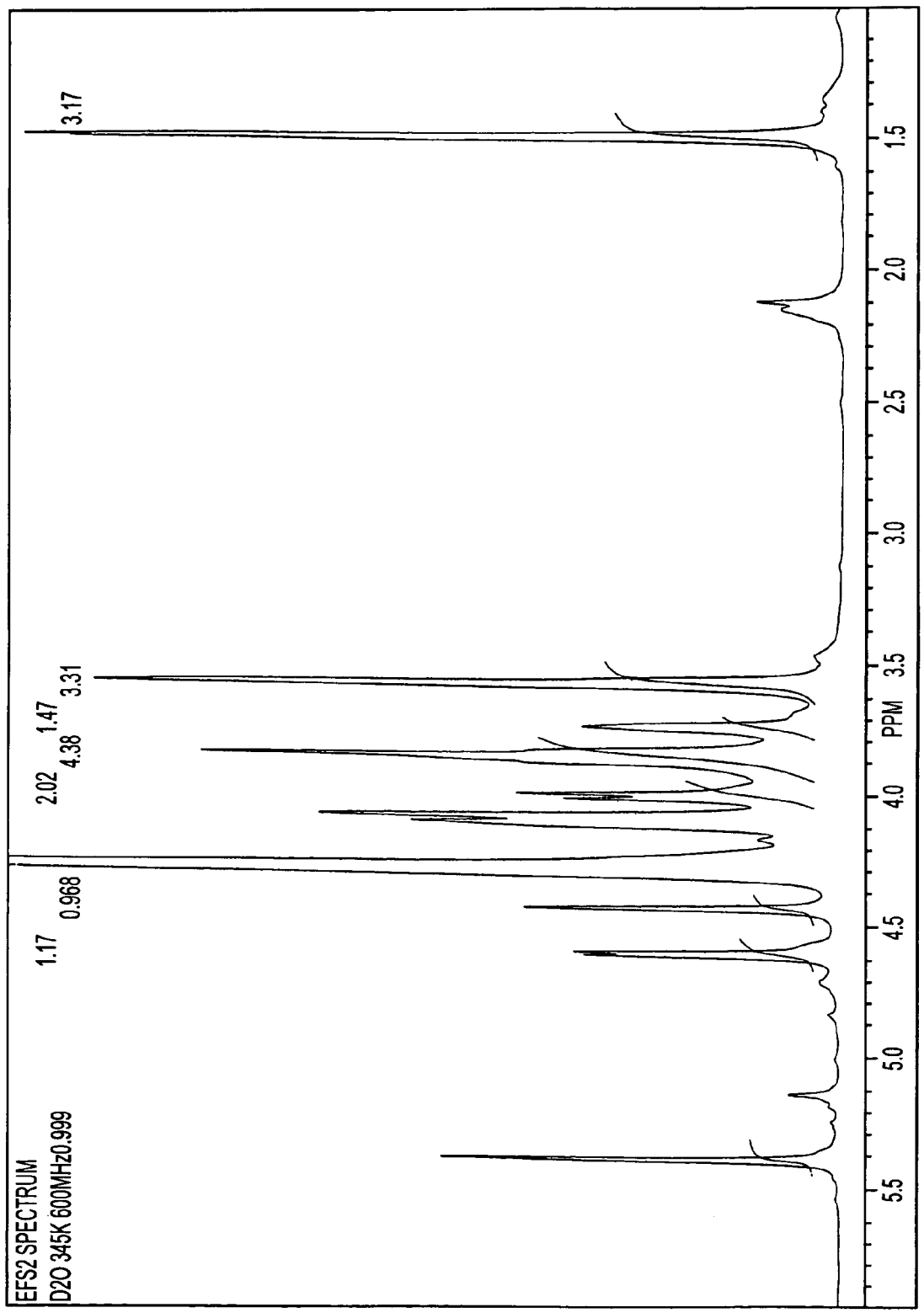

EFS2 antigen comprises a trisaccharide repeat, as determined by 1H-NMR (FIG. 2). One of the sugars is a 6-deoxy sugar. The constituent sugars do not contain N- or O-acetyl substituents. The antigen gave a positive color in phenol-sulfuric acid assay, indicating the presence of neutral sugar residues. The antigen was eluted from anion exchange column with buffer containing >0.20 M NaCl and it moved towards the anode in rocket immunoelectrophoresis, which means that it contains acidic groups.

Sugar analysis of EFM3 antigen revealed the presence of 2-acetamido-2-deoxy-galactose and galactose as the two major sugars. A complete biochemical analysis of the antigen is given in Table 2.

TABLE 2

| EFM3 | |
|---|---|
| Assay performed | Result |
| Phenol-sulfuric acid | 23-39% |
| Phosphorus | 1.12-3.6% |
| Residual nucleic acid | <1% |
| Residual protein | <2% |
| Uronic acid | undetectable |
| O-acetyl | undetectable |

Figure 3:
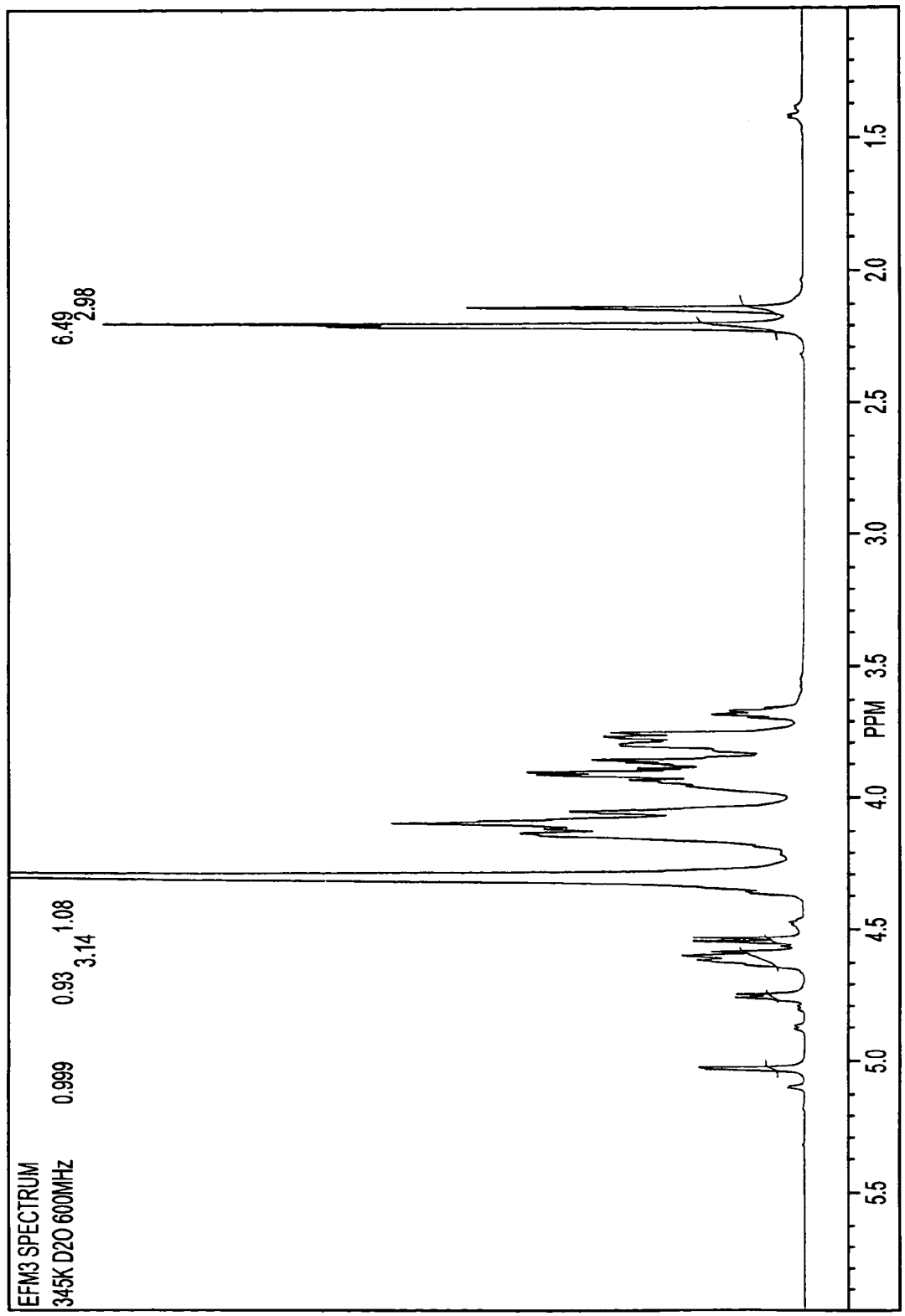

EFM3 antigen also was analyzed by H$^1$-NMR spectroscopy and the full spectrum is shown in FIG. 3. The characteristic resonances observed in the downfield region were at δ. 5.01 (s), 4.73 (d, J=7.8 Hz), 4.6-4.55, (complex) and 4.52 (d, J=7.8 Hz). Protons from N-acetyl groups resonated in the high field region at δ. 6. 2.14, 2.20 and 2.21.

EFS1 and EFS2 each reacted specifically in capillary with antisera obtained from rabbits immunized with a whole cell vaccine of ATCC 202013 and ATCC 202014, respectively. Additionally, EFS2 reacted with whole cell antisera to ATCC 202013 in capillary, due to the expression of minor amounts of EFS2 by EFS1 strains. EFS1 did not react with whole cell antisera to ATCC 202014 in capillary, and more sensitive techniques such as dot blot are required to detect the presence of EFS1 specific antibodies in EFS2 immunized rabbit sera. EFM3 antigen reacted specifically with sera from rabbits immunized with cells of ATCC 202015. EFM3 antigen did not cross react with specific antisera obtained from rabbits immunized with either ATCC 202013 or ATCC 202014.

In an in vitro assay, rabbit antisera against ATCC 202013 specifically deposited C3b component of human complement on plates coated with EFS1 antigen, and rabbit antisera against ATCC 202015 specifically deposited C3b component of human complement on plates coated with EFM3 antigen. No cross deposition of C3b occurred.

EXAMPLE 6

Preparation of Antigen-Immunocarrier Conjugates

A solution of antigen in water (10 mg/ml) was cooled in an ice-water bath. A cold aqueous solution (100 mg/ml) of 1-cyano-4-dimethylaminopyridine tetrafluoroborate (CDAP) was added to this solution, in an amount 1.2 times the volume of above antigen solution. A volume of 0.2 M aqueous triethyl amine solution equal to the volume of CDAP solution added earlier then was added dropwise. After stirring the mixture for a total of 3 minutes at 4° C., an equal volume of 0.5 M ADH solution prepared in 0.5 M sodium hydrogen carbonate was added. The above solution was stirred at 4° C. overnight, dialyzed against cold distilled water and lyophilized to obtain derivatized final product. The amount of ADH incorporated into antigen was determined calorimetrically by trinitrobenzene sulfonic acid (TNBS) assay.

Equal amounts of ADH-derivatized polysaccharide and DT were dissolved in water to obtain final concentration of 5-10 mg/ml of each component. This solution was adjusted to pH 5.6 using 0.1 M hydrochloric acid. To this solution was added a freshly prepared solution of 1-ethyl-3-(3-dimethylaminopropyl) carbodiimide (EDAC) in minimum amount of water, in an amount four times by weight of the antigen. The solution was stirred vigorously at room temperature and pH of the solution was maintained at 5.6 using 0.1 M HCL. The reaction was stopped after 1 hour by bringing the pH to 7.0 with 0.1 M NaOH. Pure conjugate was obtained by size exclusion chromatography on Sephacryl S-100 column eluted with PBS. The amount of antigen and protein in the conjugates was determined by phenol sulfuric acid assay and BCA assay using the corresponding antigen or BSA as standards, respectively.

EXAMPLE 7

Preparation of Antisera to *Enterococcus* Antigen-Immunocarrier Conjugates

White female New Zealand rabbits were immunized by subcutaneous injection with 50 μg of antigen-immunocarrier conjugate prepared according to Example 6 on days 0, 14 and 28. The first injection was given with an equal volume of complete Freund's adjuvant (CFA) and subsequent injections were given with incomplete Freund's adjuvant (IFA).

Test bleeds taken from rabbits were monitored for the presence of precipitating rabbit antibodies specific to the antigen with which they were immunized. Further injections were given as needed to boost the titer.

Rabbits were bled to obtain high titered rabbit antisera that contained antibodies specific to the antigen with which they were immunized. The antisera were used to evaluate the ability of the specific antibodies to mediate opsonophagocytosis of corresponding *Enterococcus* bacteria by HL-60 cells in in vitro assays.

Sera obtained from rabbits immunized with *E. faecalis* EFS1-DT conjugate were high titered and gave precipitates with EFS1 in capillary. The antibodies were able to mediate killing of cells carrying EFS1 by HL 60 in the presence of complement. Rabbits immunized with *E. faecium* antigen-DT conjugate were also able to elicit antigen specific antibodies. These antibodies gave precipitates with *E. faecium* antigen in capillary.

EXAMPLE 8

In Vitro Opsonophagocytosis Assays

Bacteria were transferred from stock beads to a new Todd Hewitt thioglycolate agar plate. The plate was incubated for 18-20 hours at 37° C. in 5% $CO_2$. The bacteria were scraped from the plate and suspended in two milliliters of sterile saline. The tube was centrifuged at 2000 rpm for 10 minutes at 25-35° C., and the supernatant was removed. The pelleted bacteria was resuspended in two milliliters of sterile saline, and used to prepare a suspension of bacteria of an optical density of 0.1 at 540 nm.

A 1:100 diluted sample prepared from the above-described bacterial suspension in RP-5 medium was used as working stock of bacteria solution. This bacterial preparation was tested against corresponding antisera for positive slide agglutination. The bacterial working stock was loaded into microtiter plate wells with the appropriate dilution of RP-5 medium.

PMNs were obtained from HL-60 cells adjusted to a concentration of $1.0 \times 10^7$ cells per ml in RP-5 medium. The PMN cells were centrifuged at 1000 rpm for 10 minutes at 30-35° C. The pelleted cells were resuspended in five milliliters of RP-5 medium and centrifuged at 1000 rpm for 10 minutes. The pelleted cells were resuspended in one milliliter of RP-5 medium to yield a working concentration of $1 \times 10^7$/ml.

A human complement prepared from human serum was diluted to 1:40 in RP-5 medium. The reaction mixture in the microtiter plate wells contained 50 μl of bacteria [$10^6$-$10^7$ cells/ml], 50 μl of diluted sera, 50 μl PMN [$1 \times 10^7$ cells/ml] and 50 μl of complement [1:40], to give a total volume of 200 μl. At time zero, a 20 μl sample from the reaction plate was serially diluted $10^{-1}$, $10^{-2}$, $10^{-3}$ and $10^{-4}$. A 10 μl sample from each dilution was plated onto a tryptic soy agar (TSA) plate. The TSA plates were incubated overnight 37° C., 5% $CO_2$. After the time zero dilution, the reaction plate was incubated at 370° C. for 90 minutes. The samples were remixed. A 20 μl sample from the reaction plate was serially diluted $10^{-1}$, $10^{-2}$, $10^{-3}$ and $10^{-4}$. A 10 μl sample from each dilution was plated onto a TSA plates, which then were incubated overnight 370° C., 5% $CO_2$.

The bacterial colonies were counted for each dilution/sample/plate, and percentage kill of bacteria was calculated by the formula:

$$\% \text{ kill} = \frac{\text{No. of colonies at } T_0 - \text{no. of colonies at } T_{90} \times 100}{\text{number of colonies at } T_0}$$

Both whole cell antiserum from rabbits immunized with ATCC 202013 and rabbit antibodies raised against EFS1-DT conjugates mediated the opsonophagocytosis of E. faecalis by HL-60 in the presence of human complement. Opsonic activity of anti-EFS1-DT conjugate rabbit antibodies was absorbed out completely by EFS1-DT conjugate. Opsonic activity of whole cell antisera was only partially absorbed with EFS1-DT conjugate, indicating that part of the opsonic activity of the whole cell antisera arises from antibodies directed towards an antigen other than EFS1. Opsonic activity of both anti-EFS1-DT conjugate and whole cell antibodies were completely absorbed out by ATCC 202013. Whole cell antibodies raised against ATCC 202014 did not react with EFS1 in agglutination assays, clearly indicating that EFS1 and EFS2 are distinct antigens.

Whole cell antiserum from rabbits immunized with ATCC 202014 mediated the opsonophagocytosis of E. faecalis by HL-60 in the presence of human complement. The whole cell rabbit antibodies also were able to mediate opsonophagocytosis of multiple E. faecalis isolates, including EFS1 isolates, by HL-60 in the presence of human complement. This opsonic activity could be absorbed out by the EFS2. EFS1-DT conjugate failed to absorb out the opsonic activity of whole cell antiserum from rabbits immunized with ATCC 202014. This observation suggests that the immune response elicited by EFS2 isolates in rabbits is against EFS2 antigen and that the antibodies against EFS2 antigen can mediate opsonophagocytosis of multiple E. faecalis isolates by HL-60 in the presence of human complement.

EXAMPLE 9

In Vivo Protection of Mice from E. faecalis Challenge by EFS1-DT Conjugate Antibodies A total of 42 ICR mice were divided into three groups with 15 mice in each of the first two groups and 12 mice in the third group. The mice in the first two groups were immunized with an intraperitoneal injection of 0.75 mg of protein G column-purified rabbit IgG obtained either from conjugate immunized rabbits (I-IgG) or normal rabbits (N-IgG). The third group was immunized with PBS. Twenty four hours later, all animals were challenged with $5 \times 10^7$ CFU of an EFS1 strain other than ATCC 202013, mixed with 5% hog mucin. Blood samples were taken from all the mice through their eyes at 6, 24, 48, 72 and 168 hours. These samples were plated on TSA plates and levels of bacteremia in the mice was quantitated by bacterial counts in the blood. Results are shown in Table 3.

After 48 hours, only 17% of mice were bacteremic in the I-IgG group, while in the NOIgG and PBS immunized groups the corresponding number were 60% and 79%, respectively. After 7 days, all the animals were sacrificed and their livers and kidneys were isolated and these organs were sampled for bacterial colonization. Fewer animals in the I-IgG group (4/30) had detectable bacterial colonization in the kidneys compared to the N-IgG group (9/30) or the PBS group (13/24). These observations clearly demonstrate antibodies specific to EFS1 antigen are able to protect mice from E. faecalis bacterial challenge.

TABLE 3

Bacteremia and Mouse Organ Colonization Counts
Geometric Mean of Positive Samples/Number of Positive Samples
(A positive sample has counts $\geq 10^2$ CFU/ml

| Time Post-challenge (Kind of sample) | Group 1 E1DTd-RIgG, 0.75 mg | Group 2 NR IgG, 0.75 mg | Group 3 PBS |
| --- | --- | --- | --- |
| Six Hours (Blood samples) | 2.66E+03 24/30 | 9.68E+03 30/30 | 1.33E+04 24/24 |
| Twenty-four hours (Blood samples) | 2.28E+02 12/30 | 7.91E+02 25/30 | 2.46E+03 22/24 |
| Forty-eight hours (Blood samples) | 3.72E+02 5/30 | 9.68E+02 18/30 | 3.43E+03 19/24 |
| Seventy-two hours (Blood samples) | 8.68E+02 4/30 | 1.11E+03 15/30 | 9.81E+02 16/24 |
| Six or seven days (Blood samples) | 3.86E+02 2/30 | 4.63E+02 9/30 | 3.81E+02 11/24 |
| Six or seven days (Kidney samples) | 7.48E+02 4/30 | 3.42E+02 9/30 | 1.36E+03 13/24 |
| Six or seven days (Liver samples) | 1.90E+03 18/30 | 3.59E+03 28/30 | 9.20E+03 22/24 |

What we claim is:

1. A composition comprising (i) an isolated polysaccharide E. faecalis antigen and (ii) an isolated polysaccharide E. faecium antigen, and (iii) a sterile, pharmaceutically-acceptable carrier therefore, wherein:
    said isolated polysaccharide E. faecalis antigen is different from said isolated polysaccharide E. faecium antigen, and
    said antigens are selected from the group consisting of:
    a polysaccharide E. faecalis antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
    a polysaceharide E. faecalis antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
    a polysaccharide E. faecium antigen comprising 2-acetamido-2-deoxy-galactose and galactose as its major sugar components and that specifically reacts with antibody to ATCC 20215.

2. A composition as claimed in claim 1, wherein each of said antigens further comprises an immunocarrier conjugated to said antigen.

3. A composition as claimed in claim 2, wherein each of said antigens is conjugated to the same immunocarrier.

4. A composition as claimed in claim 3, wherein said immunocarrier is a recombinantly-produced, non-toxic mutant of Pseudomonas aeruginosa exotoxin A.

5. A multivalent vaccine comprising (i) a conjugate of an immunocarrier with an antigen that specifically reacts with antibodies to ATCC 202013, (ii) a conjugate of an immunocarrier with an antigen that specifically reacts with antibodies to ATCC 202014, (iii) a conjugate of an immunocarrier with an antigen that specifically reacts with antibodies to ATCC 202015, (iv) a conjugate of an immunocarrier with an antigen that specifically reacts with antibodies to ATCC 202016, and (v) a conjugate of an immunocarrier with an antigen that specifically reacts with antibodies to ATCC 202017, and (vi) a sterile, pharmaceutically-acceptable carrier therefor.

6. An immunotherapy method comprising administering to a subject an iminunostimulatory amount of a composition comprising
(i) an *Enterococcus* antigen selected from the group consisting of:
a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215, wherein said antigen is covalently bonded to an immunocarrier, and
(ii) a sterile, pharmaceutically-acceptable carrier therefor.

7. An immunotherapy method comprising administering to a subject an immunostimulatory amount of a composition comprising (i) an isolated polysaccharide *E. foecalis* antigen and (ii) an isolated polysaccharide *E. faecium* antigen, and (iii) a sterile, pharmaceutically-acceptable carrier therefore, wherein:
said isolated polysaccharide *E. faecalis* antigen is different from said isolated polysaccharide *E. faecium* antigen;
each of said antigens further comprises an immunocarrier conjugated to said antigen;
and said antigens are selected from the group consisting of:
a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215.

8. A method of preparing an immunotherapeutic agent against *Enterococcus* infection, comprising the steps of:
(A) immunizing subjects with a composition comprising
(i) a polysaccharide *Enterococcus* antigen selected from the group consisting of:
a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetainido-2-deoxy-galactose and galactose as its major sugar components and that specifically reacts with antibody to ATCC 20215,
wherein said antigen is covalently bonded to an immunocarrier, and
(ii) a sterile, pharmaceutically-acceptable carrier therefor;
(B) collecting plasma from said immunized subjects, and
(C) harvesting an immune globulin that contains antibodies directed against *Enterococcus* from said collected plasma.

9. A method of preparing an immunotherapeutic agent against *Enterococcus* infection, comprising:
(A) immunizing subjects with a composition comprising
(i) an isolated polysaceharide *E. faecalis* antigen and
(ii) an isolated polysaccharide *E. faecium* antigen, and
(iii) a sterile, pharmaceutically-acceptable carrier therefore, wherein:
said isolated polysaccharide *E. faecalis* antigen is different from said isolated polysaccharide *E. faecium* antigen;
each of said antigens further comprises an immunocarrier conjugated to said antigen, and
said antigens are selected from the group consisting of:
a polysaceharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215;
(B) collecting plasma from said immunized subjects, and
(C) harvesting an immune globulin that contains antibodies directed against *Enterococcus* from said collected plasma.

10. An isolated immune globulin containing antibodies directed against an *Enterococcus* antigen selected from the group consisting of:
a polysaceharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215.

11. An immune globulin as claimed in claim 10, containing a monoclonal antibody directed against a polysaccharide

*E. faecalis* antigen and a monoclonal antibody directed against a polysaccharide *E. faecium* antigen.

12. An isolated immune globulin containing antibodies directed against both a polysaceharide *E. faecalis* antigen and a polysaccharide *E. faecium* antigen, wherein said polysaccharide *E. faecalis* antigen is different from said polysaccharide *E. faecium* antigen, and wherein said antigens are selected from the group consisting of:
   a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
   a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
   a polysaccharide *E. faecium* antigen comprising 2-acetamido-2-deoxy-galactose and galactose as its major sugar components and that specifically reacts with antibody to ATCC 20215.

13. An immunotherapy method comprising administering to a subject an immune globulin containing antibodies directed against an *Enterococcus* antigen selected from the group consisting of:
   a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
   a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
   a polysaccharide *E. faecium* antigen comprising 2-acetamido-2-deoxy-galactose and galactose as its major sugar components and that specifically reacts with antibody to ATCC 20215.

14. An immunotherapy method comprising administering to a subject an immune globulin containing antibodies directed against an *Enterococcus* antigen selected from the group consisting of:
   a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
   a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
   a polysaccharide *E. faecium* antigen comprising 2-acetamido-2-deoxy-galactose and galactose as its major sugar components and that specifically reacts with antibody to ATCC 20215,
   wherein said immune globulin contains a monoclonal antibody directed against an *E. faecalis* polysaccharide antigen and a monoclonal antibody directed against an *E. faecium* polysaccharide antigen.

15. An isolated antibody to an *Enterococcus* antigen selected from the group consisting of:
   a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
   a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
   a polysaccharide *E. faecium* antigen comprising 2-acetamido-2-deoxy-galactose and galactose as its major sugar components and that specifically reacts with antibody to ATCC 20215.

16. A monoclonal antibody to an isolated *Enterococcus* antigen selected from the group consisting of:
   a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
   a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
   a polysaccharide *E. faecium* antigen comprising 2-acetamido-2-deoxy-galactose and galactose as its major sugar components and that specifically reacts with antibody to ATCC 20215.

17. A diagnostic assay for detecting the presence of anti-*Enterococcus* antibody in a sample, comprising the steps of:
   mixing
   (i) an *Enterococcus* antigen selected from the group consisting of:
      a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
      a polysaceharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
      a polysaccharide *E. faecium* antigen comprising 2-acetamido-2-deoxy-galactose and galactose as its major sugar components and that specifically reacts with antibody to ATCC 20215, with
   (ii) a sample suspected of containing *Enterococcus*-specific antibody; and detecting any binding between said antigen and any *Enterococcus*-specific antibody in said sample.

18. A diagnostic assay as claimed in claim 17, wherein said antigen is immobilized on a solid matrix.

19. A diagnostic assay for detecting the presence of *Enterococcus* antigen in a sample, comprising the steps of:
mixing
(i) an isolated antibody to an *Enterococcus* antigen selected from the group consisting of:
a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215, with
(ii) a sample suspected of containing *Enterococcus* antigen; and detecting any binding between said antibody and any *Enterococcus* antigen in said sample.

20. A diagnostic assay as claimed in claim 19, wherein said antibody is immobilized on a solid matrix.

21. A kit for detecting the presence of *Enterococcus* antigen in a sample, comprising:
a monoclonal *Enterococcus* antibody that specifically binds to one of ATCC 202013, ATCC 202014, ATCC 202015, ATCC 202016, and ATCC 202017, the monoclonal antibody being labeled with a radioisotope label or an enzyme label; and
instructions for carrying out a diagnostic assay comprising the steps of mixing said monoclonal *Enterococcus* antibody with a sample suspected of containing *Enterococcus* antigen and detecting any binding between said antigen and said antibody in said sample.

22. A kit as claimed in claim 21, wherein the kit further comprises a solid matirix and wherein said antibody is immobilized on a said solid matrix.

23. A diagnostic assay for detecting the presence of anti-*Enterococcus* antigen in a sample, comprising the steps of:
mixing
(i) a monoclonal *Enterococcus* antibody to an isolated *Enterococcus* antigen selected from the group consisting of:
a polysaccharide *E. faecalis* antigen comprising 2-acetamido-2-deoxy-glucose, rhamnose, glucose, and 2-acetamido-2-deoxy-galactose in a 1:2:2:2 molar ratio as its major sugar groups and that specifically reacts with antibody to ATCC 20213;
a polysaccharide *E. faecalis* antigen comprising a trisaccharide repeat that comprises a 6-deoxy sugar and that does not comprise sugars with N-acetyl or O-acetyl substituents, wherein the antigen further comprises acidic groups and specifically reacts with antibody to ATCC 20214; and
a polysaccharide *E. faecium* antigen comprising 2-acetamido-2-deoxy-galactose and galactose as its major sugar components and that specifically reacts with antibody to ATCC 20215
with
(ii) a sample suspected of containing *Enterococcus* antigen; and detecting any binding between said antibody and any *Enterococcus* antigen in said sample.

24. A diagnostic assay as claimed in claim 23, wherein said antibody is immobilized on a solid matrix.

* * * * *